United States Patent [19]

Olejnik et al.

[11] Patent Number: 5,733,938
[45] Date of Patent: Mar. 31, 1998

[54] COMBINATION OF LEVOBUNOLOL AND DIPIVEFRIN FOR TOPICAL OPHTHALMIC USE

[75] Inventors: Orest Olejnik, Trabuco Canyon, Calif.; Gary D. Novack, Irvine, Calif.

[73] Assignee: Allergan, Waco, Tex.

[21] Appl. No.: 303,850

[22] Filed: Sep. 9, 1994

[51] Int. Cl.⁶ .................................................. A61K 31/135
[52] U.S. Cl. ............................ 514/652; 514/653; 514/913
[58] Field of Search .................................. 514/652, 653, 514/913

[56] References Cited

PUBLICATIONS

Medline Abstract of Journal of Ophamology, 106 (7), pp. 904–907, (1988).

*Primary Examiner*—Zohreh Fey
*Attorney, Agent, or Firm*—Robert J. Baran; Martin A. Voet; Howard R. Lambert

[57] ABSTRACT

Disclosed are pharmaceutical compositions comprising dipivefrin and levobunolol for topical ophthalmic delivery and a method of treatment comprising administering said composition when indicated for glaucoma and associated conditions such as elevated intraocular pressure in the eyes of humans.

4 Claims, No Drawings

COMBINATION OF LEVOBUNOLOL AND DIPIVEFRIN FOR TOPICAL OPHTHALMIC USE

BACKGROUND OF THE INVENTION

This invention relates to the topical ophthalmic use of a sympathomimetic agent in combination with an adrenergic agent when indicated for treatment of glaucoma. Such combinations or formulations are available for separate use in the ophthalmic art and have been combined in serial application during the course of treatment of glaucoma. However, there are concerns and expressed reservations in the ophthalmic community about patient compliance when the patient is required to administer separate medications to treat a single disease or condition such as glaucoma. There is, moreover a long felt need for an effective and safe topical ophthalmic pharmaceutical composition including a sympathomimetic agent and an adrenergic agent which has increased stability and requires a lower effective concentration of preservative as compared to the individual agents taken alone. Finally, there is a need to increase the penetration of many topical ophthalmic agents, since it is well known that the penetration of many of such topically-applied ophthalmic agents is insubstantial and results in limited efficacy. Unexpectedly it has been discovered that levobunolol in combination with dipivefrin meets these criteria.

Levobunolol is disclosed in U.S. Pat. No. 3,649,691.

Dipivefrin is disclosed in U.S. Pat. No. 3,809,714 and the use of dipivefrin as an antiglaucoma agent is disclosed in U.S. Pat. No. 3,839,584.

DESCRIPTION OF THE INVENTION

Levobunolol is reported to be a non selective β adrenoceptor antagonist represented by the following formula:

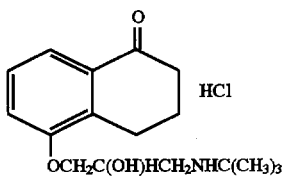

OCH₂C(OH)HCH₂NHC(CH₃)₃

Dipivefrin is a sympathomimetric agent represented by the following formula:

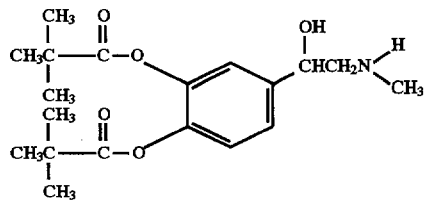

Both of these compounds are available from Allergan, Inc., Irvine, Calif. as separate ophthalmic pharmaceutical products having the names Betagan® and Propine®, respectively.

The compositions of the present invention are administered topically. The dosage is 0.001 to 5.0 mg/per eye; wherein the cited mass figures represent the sum of the two components, levobunolol and dipivefrin. The compositions of the present invention can be administered as solutions in a suitable ophthalmic vehicle.

In many instances, the lipophilic-hydrophilic balance of an ophthalmic agent, expressed as its partition coefficient, is altered to achieve enhanced penetration across the cornea. The three predominant techniques in achieving this is either through the synthesis of a pro-drug, pH-drug ionization manipulation, or ion-pair formation. In each case specific requirements must be met for improved transport across the cornea to occur.

For levobunolol and dipivefrin manipulation of the solution milieu to achieve enhanced penetration of each agent is limited. However, it was surprisingly found that by having the two compounds in combination and in solution, resulted in an enhanced efficacy. This was an unusual event since under controlled conditions of pH, ionic strength, osmolality and viscosity no change in the thermodynamic activity of levobunolol or dipivefrin was predicted. Moreover, the absence of ion-pairing sites between the two drug compounds ruled out any potential for increased corneal penetration through ion-pair formation. While not wishing to be bound by theory, it is believed that a modification of the hydrophobic character of both levobunolol and dipivefrin occurs as a result of their own intrinsic activity upon each other. It is further believed that the presence of both levobunolol and dipivefrin preferentially influenced each other's partition coefficient, through water structuring, a concept proposed by Diamond 1963; R. M. Diamond J. Phys. Chem. 67, 2513), thus facilitating complexation phenomenon between the two compounds and eliciting an overall increase in the partition coefficient.

In forming compositions for topical administration, the mixtures are preferably formulated as 0.01 to 2.0 percent by weight solutions in water at a pH of 4.5 to 8.0 (figures relate to combined presence of levobunolol and dipivefrin. While the precise regimen is left to the discretion of the clinician, it is recommended that the resulting solution be topically applied by placing one drop in each eye two times a day.

Other ingredients which may be desirable to use in the ophthalmic preparations of the present invention include preservatives, co-solvents and viscosity building agents.

Antimicrobial Preservative:

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium sorbic acid, Onamer M, or other agents known to those skilled in the art. Typically such preservatives are employed at a level of from 0.001% to 1.0% by weight. It has been found that a concentration of benzalkonium chloride of 0.005% is sufficient to preserve the compositions of the present invention from microbial attack. This concentration may be advantageously compared to the requirement of 0.004% benzalkonium chloride to preserve levobunolol and 0.005% benzalkonium chloride to preserve dipivefrin in the individual, commercially-available ophthalmic products.

Co-Solvents:

The solubility of the components of the present compositions may be enhanced by a surfactant or other appropriate co-solvent in the composition. Such co-solvents include polysorbate 20, 60, and 80, Pluronic F-68, F-84 and P-103, cyclodextrin, or other agents known to those skilled in the art. Typically such co-solvents are employed at a level of from 0.01% to 2% by weight.

Viscosity Agents:

Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Such viscosity building agents include as examples polyvinyl alcohol, polyvinyl pyrrolidone, methyl cellulose, hydroxypropyl methylcellulose, hydroxyethyl cellulose, carboxymethyl cellulose, hydroxy propyl cellulose or other agents known to those skilled in the art. Such agents are typically employed at a level of from 0.01% to 2% by weight.

The present invention further comprises an article of manufacture comprising packaging material and a pharmaceutical agent contained within said packaging material, wherein the pharmaceutical agent is therapeutically effective for lowering intraocular pressure and wherein the packaging material comprises a label which indicates the packaging material can be used for lowering intraocular pressure and wherein said pharmaceutical agent comprises effective amount of levobunolol and an effective amount of dipivefrin.

The following example is a representative pharmaceutical composition of the invention for topical use when indicated for treating glaucoma.

EXAMPLE I

| Levobunolol Hydrochloride | 0.500 |
|---|---|
| Dipivefrin Hydrochloride | 0.105 |
| Benzalkonium Chloride | 0.0050 |
| Edetate Disodium | 0.015 |
| Sodium Chloride | 0.74 |
| Polyvinyl Alcohol, 20–90 | 1.40 |
| Dilute Hydrochloride Acid and/or dilute Sodium Hydroxide | q.s. pH to 3.4–3.6 |
| Purified Water | q.s.-ad |

EXAMPLE II

In a clinical study of 214 patients, the dipivefrin HCl 0.1% Levobunolol HCl 0.5% combination (DPEL) of Example 1 decreased IOP significantly more than either dipivefrin (DPE) or levobunolol (LBUN) administered separately (DPEL vs. LBUN p=0.042 and vs. DPE p=0.006). A mean decrease of at least 3 mm Hg from baseline was achieved in 44% of patients with DPEL and only in 22% with DPE (p=0.018) and 24% with LBUN (p=0.045).

The invention has been described herein by reference to certain preferred embodiments. However, as obvious variations thereon will become apparent to those skilled in the art, the invention is not to be considered as limited thereto.

We claim:

1. An ophthalmic pharmaceutical composition useful in the treatment of glaucoma comprising an effective amount of dipivefrin and an effective amount of levobunolol and a pharmaceutically acceptable carrier therefore, said composition having a pH in the range of 3.4 and 3.6.

2. A composition according to claim 1, wherein the concentration of the dipivefrin, as dipivefrin HCl, is 0.1 percent by weight and the concentration of the levobunolol, as levobunolol HCl, is 0.5 percent by weight.

3. A method of treating glaucoma which comprises administering a therapeutically effective amount of a composition according to claim 1 topically to the affected eye.

4. A method of lowering intraocular pressure which comprises administering a therapeutically effective amount of a composition according to claim 2 to the affected eye.

* * * * *